US005125241A

United States Patent [19]

Nakanishi et al.

[11] Patent Number: 5,125,241

[45] Date of Patent: Jun. 30, 1992

[54] REFRIGERATING APPARATUS HAVING NOISE ATTENUATION

[75] Inventors: Keiji Nakanishi, Takatsuki; Yasuyuki Sekiguchi, Ibaraki, both of Japan

[73] Assignee: Kabushiki Kaisha Toshiba, Kawasaki, Japan

[21] Appl. No.: 666,049

[22] Filed: Mar. 7, 1991

[30] Foreign Application Priority Data

Mar. 12, 1990 [JP] Japan .................................... 2-60830
Mar. 13, 1990 [JP] Japan .................................... 2-61712

[51] Int. Cl.[5] ........................ F25D 19/00; A61F 11/06

[52] U.S. Cl. ........................................ 62/296; 381/71; 417/14

[58] Field of Search ............... 381/71, 94, 73; 62/296; 417/14

[56] References Cited

U.S. PATENT DOCUMENTS 4,527,282 7/1985 Chaplin et al. ........................ 381/71
4,989,252 1/1991 Nakanishi et al. .................... 381/71
5,010,739 4/1991 Isshiki et al. .......................... 62/158

FOREIGN PATENT DOCUMENTS 8907701 8/1989 World Int. Prop. O. ............ 381/71

*Primary Examiner*—William E. Wayner
*Attorney, Agent, or Firm*—Cushman, Darby & Cushman

[57] ABSTRACT

A refrigerator with a noise attenuating function includes a cabinet having storage and machine compartments, a compressor disposed in the machine compartment, a noise detector disposed in the machine compartment for detecting noise produced from driving of the compressor and converting the noise to an electrical signal, an operational unit for converting the electrical signal to an acoustic signal for an active noise control, a cancellation sound producer producing a sound of opposite phase with the noise based on the acoustic signal so that the noise is attenuated, a noise attenuation monitoring sound receiver for monitoring the noise attenuating effect of the cancellation sound producer, an adaptive control circuit changing an operational factor of the operational unit by a predetermined amount when the monitoring result of the noise attenuation monitoring sound receiver is out of a predetermined tolerance, the adaptive control circuit being adapted to continuously perform the operation of changing the operational factor until the monitoring result comes into the tolerance, and a connecting member for integrally connecting the cancellation sound producer and the noise attenuation monitoring sound receiver.

7 Claims, 6 Drawing Sheets

REFRIGERATING APPARATUS HAVING NOISE ATTENUATION

BACKGROUND OF THE INVENTION

This invention relates to a refrigerating apparatus such as a household refrigerator provided with a noise attenuating function actively attenuating noise produced from a compressor of the refrigerator or the like.

Almost every home is generally furnished with a refrigerating apparatus employing a compressor, for example, a household refrigerator. Since such a refrigerator is in continuous operation throughout the year, it is important to solve a problem of noise produced therefrom. In the refrigerator, one critical noise source is a machine compartment enclosing a compressor and piping system connected to the compressor. More specifically, from the machine compartment emanates a relatively loud noise, for example, a noise produced from driving of a compressor motor, noise produced from the flow of a compressed gas and mechanical noise produced by moving members of a compression system. Furthermore, the piping system connected to the compressor produces noise due to vibration thereof. The noises emanating from the machine compartment thus account for a large part of the noise of the refrigerator. Accordingly, control of the noise from the machine compartment contributes to noise reduction in the refrigerator.

Conventionally, compressors of the low noise type such as a rotary compressor have been employed for the purpose of reducing the noise emanating from the machine compartment. Further, the construction of vibration-proofing of the compressor has been improved and the configuration of the piping has been improved, thereby providing damping of the vibration in a vibration transfer path. Further, noise absorptive and insulative members have been disposed around the compressor and piping system, thereby improving an amount of noise absorbed in the machine compartment and a noise transfer loss.

However, a plurality of ventilating openings are formed in one or more walls defining the machine compartment for ventilating the machine compartment, and the noise produced in the machine compartment leaks outward through the ventilating openings. As the result of the provision of the ventilating openings, the above-mentioned conventional noise-reduction methods each have a definite limit and provide at most noise reduction of 2 dB.

With the advancement of applied electronic techniques including sound data processing circuitry and acoustic control techniques, application of an active noise control system wherein noise is attenuated by the effect of sound wave interference has recently been taken into consideration. More specifically, in the above-mentioned active noise control system, detection means such as a microphone is provided at a specific position in the machine compartment for receiving sound emanating from a noise source and converting the received noise to a corresponding electrical signal. The electrical signal is then processed to a cancellation signal by an operational unit. The cancellation signal is supplied to a cancellation sound producer such as a speaker so that an artificial cancellation sound of opposite phase or 180° out of phase with the noise received by the microphone and having the same frequency and amplitude as that of the received noise is produced by the speaker, so that the artificial sound interferes with the received noise, thereby attenuating the noise.

When the above-described active noise control system is put to a practical use, it is necessary to compensate for variations of characteristics of a noise attenuating signal system due to both aged deterioration of parts composing the signal system and the ambient temperature. For this purpose, it is proposed that an operational factor or acoustical transfer function be compensated for in accordance with variations of the noise attenuating capability of the active noise control system. To perform such a compensation, it is proposed that a noise attenuation monitoring sound receiver such as a microphone be provided for monitoring a sound attenuation effect of the control sound producer and that control means is provided for changing the operational factor of the operational unit by a predetermined amount when the monitoring result shows that the operational factor is out of a predetermined tolerance. The control means is adapted to continuously perform the operation of changing the operational factor until the operational factor comes into the tolerance. Such a control is referred to as an adaptive control wherein the noise attenuation effect in the active noise control is maintained at an optimum level.

To perform a desirable adaptive control, the noise attenuation monitoring sound receiver needs to be disposed away from the cancellation sound producer accurately by a preselected distance. Actually, however, variations in the distance between the monitoring sound receiver and the cancellation sound producer during assembly steps, which reduces the accuracy of the adaptive control. When the assembly accuracy is improved such that the variations in the distance between the monitoring sound receiver and the cancellation sound producer can be ignored, the accuracy of jigs used to mount the receiver and producer needs to improved and a careful assemblage is needed, resulting in lowered working efficiency and increased production cost.

SUMMARY OF THE INVENTION

Therefore, an object of the present invention is to provide a refrigerating apparatus provided with a noise attenuating function wherein the noise produced from driving of the compressor is actively attenuated, the noise attenuating operation is controlled in the manner of the adaptive control based on the monitoring result of the noise attenuation monitoring sound receiver, the accuracy in the positional relationship between the cancellation producer and the monitoring sound receiver can be readily improved without using specific jigs, and the accuracy in the active noise control can be improved with the improvement of the assembling efficiency and the cost reduction.

To achieve the above-described object, the present invention provides a refrigerating apparatus with a noise attenuating function comprising a heat-insulative cabinet having a storage compartment and a machine compartment, a compressor provided in the machine compartment, sound detection means provided in the machine compartment for detecting noise produced from driving of the compressor and converting the detected noise to a corresponding electrical signal, an operational unit for converting the electrical signal to an acoustic signal for an active noise control, a cancellation sound producer producing a sound of opposite phase with the noise based on the acoustic signal so that the noise is attenuated, a noise attenuation monitoring sound receiver for monitoring a noise attenuating effect of the cancellation sound producer, an adaptive control circuit changing an operational factor of the operational unit by a predetermined amount when the monitoring result of the noise attenuation monitoring sound receiver is out of a predetermined tolerance, the adaptive control circuit being adapted to continuously perform the operation of changing the operational factor until the monitoring result comes into the tolerance, and a connecting member for integrally connecting the cancellation sound producer and the noise attenuation monitoring sound receiver.

Since the cancellation sound producer and noise attenuation monitoring sound receiver are integrally connected by the connecting member, they may be built into the refrigerating apparatus without using any specific jig with a predetermined positional relationship therebetween exactly maintained, which prevents occurrence of variations in the distance between them and improves the accuracy of the adaptive control.

Preferably, the machine compartment may have a rear cover detachably mounted thereon so that a rear opening of the compartment is closed and the rear cover may also serve as the connecting member for integrally connecting the cancellation sound producer and the noise attenuation monitoring sound receiver. Upon detachment of the rear cover from the machine compartment, the cancellation sound producer and the noise attenuation monitoring sound receiver may also be detached with the rear cover. This construction is advantageous in that the inspection, repair and replacement of these members may be performed with ease.

It is preferable that the cancellation sound producer be embedded in an insulative wall defining the machine compartment. Since the cancellation sound producer can be rigidly secured by the machine compartment wall, frequency characteristics of the cancellation sound produced by the same can be improved.

It is also preferable that the sound detection means comprise a vibration sensor mounted on the compressor. Since the noise produced from driving of the compressor as a noise source can be directly sensed by the vibration sensor, the accuracy of the noise detection can be improved.

It is further preferable that one of dimensions of the machine compartment in the directions of the length, height and width thereof be set at a value larger than those of the others such that a standing wave of the sound is composed only in said one direction. In this construction, the noise produced in the machine compartment may be considered a one-dimensional plane traveling wave and consequently, the theoretical handling of the noise in the active noise control can be simplified.

It is further preferable that the rear cover of the machine compartment have a ventilating opening formed therein so as to be away from the compressor and the noise attenuation monitoring sound receiver be disposed in the vicinity of the ventilating opening in the machine compartment. In this construction, the noise attenuating effect can be improved.

It is further preferable that the rear cover of the machine compartment be formed of a material having fine heat-conductivity and large sound-transfer loss property. This construction improves the heat radiating effect and prevents the noise leakage from the rear cover.

Other objects of the present invention will become obvious upon understanding of the illustrative embodiment about to be described or will be indicated in the appended claims. Various advantages not referred to herein will occur to one skilled in the art upon employment of the invention in practice.

DESCRIPTION OF THE PREFERRED EMBODIMENTS

Figure 4:
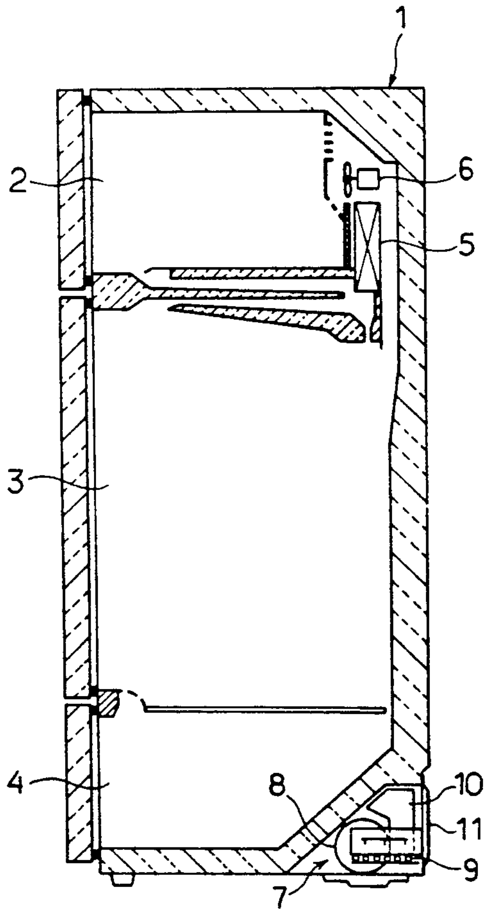
FIG. 4 is a longitudinal section of a refrigerator to which the active noise attenuation system is applied.

An embodiment in which the present invention is applied to a refrigerator will be described with reference to the accompanying drawings. Referring first to FIG. 4 showing an overall construction of the refrigerator, reference numeral 1 designates a heat-insulative cabinet of the refrigerator. The interior of the refrigerator cabinet 1 is partitioned to a freezing compartment 2, a storage compartment 3 and a vegetable compartment 4 successively from the top. An evaporator 5 is provided at the backside of the freezing compartment 2. A fan 6 is provided for directly supplying a chilled air to the freezing and storage compartments 2, 3. A machine compartment 7 is provided at the lower backside of the refrigerator cabinet 1. The machine compartment 7 encloses a rotary type compressor 8, a condenser pipe 9 and a defrost-water vaporizer 10 employing ceramic fins. During driving of the compressor 8, a refrigerant from the compressor 8 is supplied through a refrigerant path (not shown) to the evaporator 5 which evaporates the refrigerant and the fan 6 is driven so that the heat exchange is performed between the evaporator 5 and the refrigerator interior.

Figure 5:
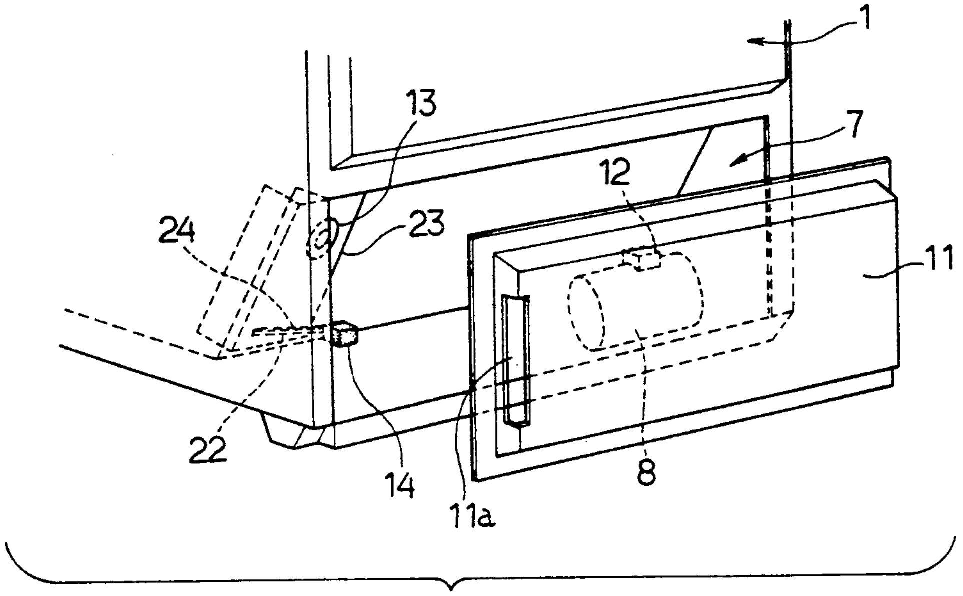
FIG. 5 is an exploded perspective view of a machine compartment of the refrigerator.

As shown in FIG. 5 wherein the condenser pipe 9 and defrost-water vaporizer 10 are eliminated, the machine compartment 7 has at the backside a generally rectangular opening which is closed by a machine compartment cover 11. In closing the opening of the machine compartment 7, the periphery of the cover 11 is air-tightly attached against the opening edge of the machine compartment 7. A generally slenderly rectangular ventilating opening 11$a$ extending vertically is formed in the left-hand edge portion of the cover 11, as viewed in FIG. 5. Thus, when the cover 11 is attached to the machine compartment 7, it is closed except the ventilating opening 11$a$. The cover 11 is formed of a hard material having good heat-conductivity and large sound-transfer loss properties, such as a metal like steel.

Further referring to FIG. 5, a vibration sensor 12 serving as sound detecting means is mounted on the compressor 8 for detecting a vibrational sound produced from the compressor with vibration thereof and converting the detected sound to a corresponding electrical signal. A speaker 13 serving as a cancellation sound producer is provided in the machine compartment 7. The speaker 13 is, for example, mounted in a portion of a machine compartment inner wall corresponding to the bottom wall of the refrigerator cabinet 1, the portion being in the vicinity of the ventilating opening 11$a$, as will be described later. A microphone 14 serving as a noise attenuation monitoring sound receiver is disposed in the vicinity of the ventilating opening 11$a$, as will be described later. The microphone 14 is adapted to receive an interference sound caused by the interference of the noise from the compressor 8 and the cancellation sound from the speaker 13 for monitoring the noise attenuation effect of the sound from the speaker 13.

Figure 1:
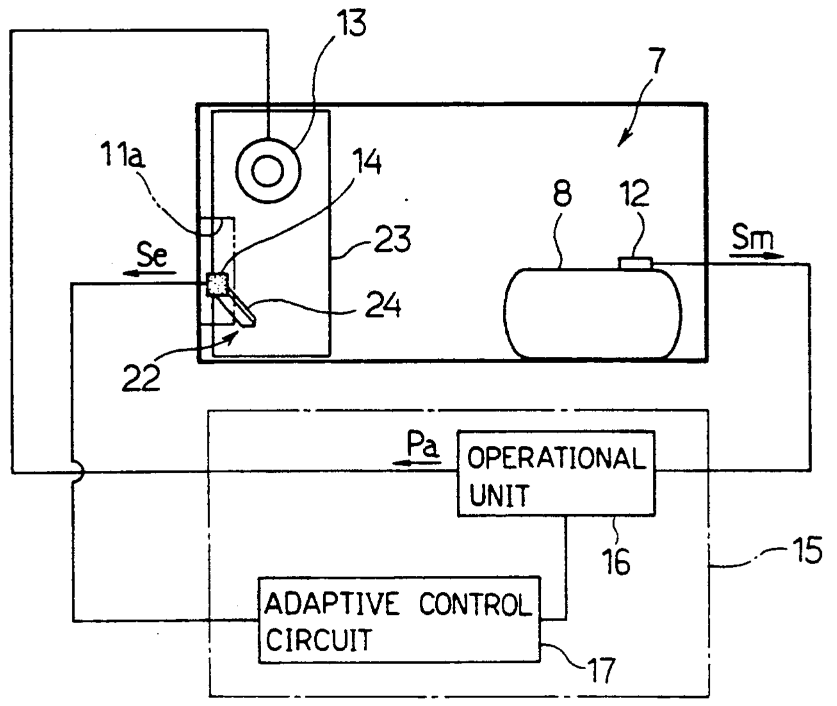
FIG. 1 schematically illustrates an active noise attenuation system of an embodiment of the invention.
Figure 6:
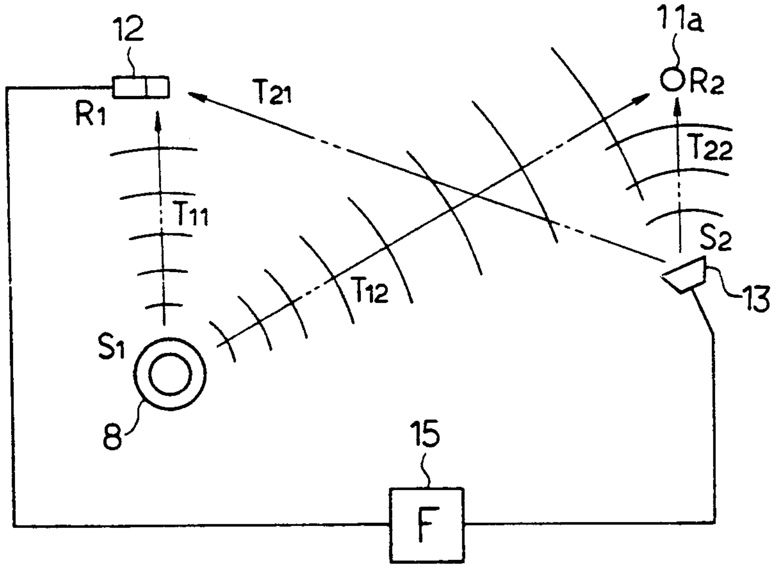
FIG. 6 schematically illustrates the noise attenuation principle by the active noise control.

Referring to FIG. 1, the electrical signal $S_m$ generated by the vibration sensor 12 is processed by an operational unit 16 in an opposite phase sound producing circuit 15 into a control signal $P_a$, which signal is supplied to the speaker 13 for activating the same. The above-mentioned processing of the electrical signal $S_m$ is performed based on the following principle of the noise attenuation by the active noise control: referring to FIG. 6, the following equation holds for two-input and two-output system:

$$\begin{bmatrix} R_1 \\ R_2 \end{bmatrix} = \begin{bmatrix} T_{11} & T_{21} \\ T_{12} & T_{22} \end{bmatrix} \begin{bmatrix} S_1 \\ S_2 \end{bmatrix}$$

where $S_1$ = sound produced from the compressor 8

$S_2$ = sound produced from the speaker 13

$R_1$ = vibrational sound sensed by the vibration sensor 12

$R_2$ = *sound received by the microphone* 14 *disposed at the ventilating opening* 11$a$ as a control point $T_{11}$, $T_{21}$, $T_{12}$, $T_{22}$ = acoustic transfer functions between input and output points of the respective sounds Accordingly, the sound $S_2$ to be produced from the speaker 13 is obtained from the following equation:

$$S_2 = (-T_{12} \cdot R_1 + T_{11} \cdot R_2)/(T_{11} \cdot T_{22} - T_{12} \cdot T_{21})$$

Since the goal is to reduce the acoustic level at the control point to zero, zero is substituted for $R_2$ as follows:

$$S_2 = R_1 \cdot T_{12}/(T_{12} \cdot T_{21} - T_{11} \cdot T_{22})$$

As is understood from this equation, in order to render $R_2$ zero, the sound $R_1$ detected by the vibration sensor 12 may be processed by a filter expressed by the following equation:

$$F = T_{12}/(T_{12} \cdot T_{21} - T_{11} \cdot T_{22}) \quad (1)$$

When a processed sound $S_2$ thus obtained is produced from the speaker 13, the sound level at the ventilating opening 11$a$ can be theoretically rendered zero. The operational unit 16 is adapted to perform the above-described sound processing at a high speed and supply a control signal Pa to the speaker 13.

Substituting G, $G_{so}$, $G_{am}$, $G_{sm}$ and $G_{ao}$ for F, $T_{12}$, $T_{21}$, $T_{11}$ and $T_{22}$ in the equation (1), respectively, $$G = G_{so}/(G_{so} \cdot G_{am} - G_{sm} \cdot G_{ao}) \quad (2)$$

In the equation (2), each first subscript in $G_{so}$, $G_{am}$, $G_{sm}$ and $G_{ao}$ denotes an input side and each second subscript an output side or response side. For example, $G_{am}$ represents an acoustic transfer function in the case where an input signal to the speaker 13 is the input side and an output signal from the microphone 14 the output side. Since the sound from the speaker 13 is not received by the vibration sensor 12 in the arrangement that the noise from the compressor 8 is detected by the vibration sensor 12, $G_{am}$ can be considered zero. Accordingly, the equation (2) is represented as follows:

$$G = -G_{so}/(G_{sm} \cdot G_{ao}) \quad (3)$$

Since $G_{so}/G_{sm} = G_{mo}$, the equation (3) is represented as follows:

$$G = -G_{mo}/G_{ao} \quad (4)$$

That is, when the sound obtained by processing the electrical signal from the vibration sensor 12 by use of a filter corresponding to G represented by the equation (4) is produced from the speaker 13, an acoustic level at the ventilating opening 11$a$ can be theoretically rendered zero.

Figure 8:
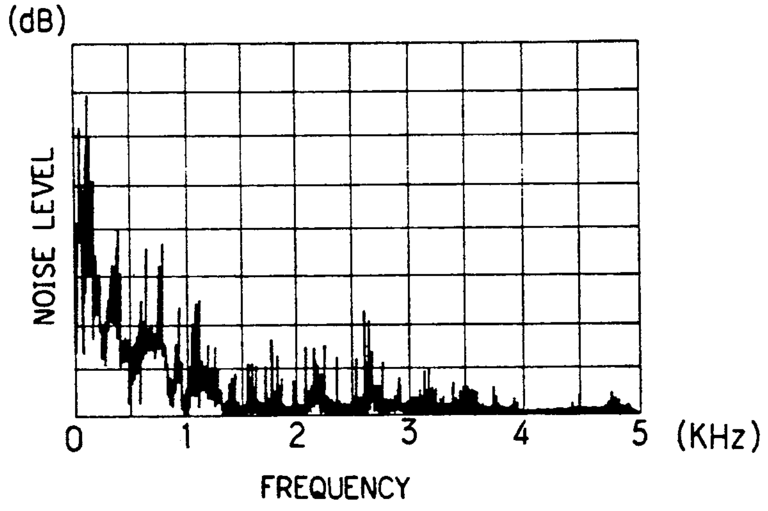
FIG. 8 is a graph showing noise level characteristics of the noise produced from driving of the compressor.

When the compressor 8 in the refrigerator constructed as described above is driven, the noise level in the machine compartment 7 has a characteristic that the noise level is increased in the frequency band below 700 Hz and in the frequency bands between 1.5 and 5 kHz, as shown in FIG. 8. Of the noises in the respective frequency bands, the high frequency noise can be damped by way of the acoustic transfer loss through the machine compartment cover 11 and the like and readily dissipated by providing a sound absorption member in the machine compartment 7. Accordingly, the active noise control by way of the vibration sensor 12, speaker 13 and operational unit 16 is aimed at the noise having frequencies below 700 Hz.

Figure 7:
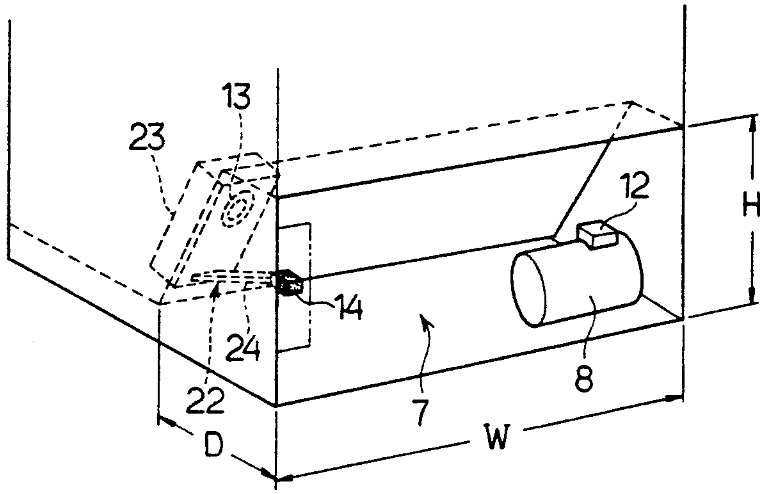
FIG. 7 is a schematically perspective view of the machine compartment for explaining the dimensions thereof.

In performing the above-described active noise control, it is important that the machine compartment 7 be constructed so that the noise in the compartment is composed to be a one-dimensional plane traveling wave, whereby the noise control is performed with ease and accuracy theoretically and technically. In the embodiment, for example, the width W or transverse dimension of the machine compartment 7 is determined so as to take a value larger than those of the depth D or front-to-back dimension and the height H or longitudinal dimension thereof, as shown in FIG. 7. More definitely, the width W is determined to be 600 mm and each of the depth D and height H is determined to be 200 mm. In other words, the dimension of the width W is approximated to the wavelength of the noise to be attenuated and the dimensions of the depth and height are rendered shorter than the wavelength of the noise to be attenuated such that a standing wave of the noise in the machine compartment 7 holds only for a primary mode. When the machine compartment 7 is considered a rectangular cavity, for example, the following equation holds:

$$f = C\sqrt{(N_x/L_x)^2 + (N_y/L_y)^2 + (N_z/L_z)^2}/2$$

where
f=resonant frequency (Hz)
$N_x$, $N_y$, $N_z$=ordinal modes in the directions of X, Y and Z, respectively
$L_x$, $L_y$, $L_z$=dimensions in the directions of X, Y and Z in the machine compartment 7, that is, D, W and H, respectively
C=sound velocity Frequencies $f_x$, $f_y$ and $f_z$ of a first standing wave in the respective directions of X, Y and Z can be obtained from the above equation. More specifically, when the depth D is determined to be 200 mm with the width W and height H 600 mm and 200 mm, respectively, the frequency $f_x$ of the first standing wave of a fundamental wave in the direction of X can be obtained as:

$$\begin{aligned} f_x &= 340\sqrt{(1/0.2)^2}/2 \\ &= 850 \text{ Hz} \end{aligned}$$

where
$N_y = N_z = 0$
C=340 m/sec

Similarly, the frequencies $f_y$ and $f_z$ of the first standing wave of the fundamental wave in the respective directions of Y and Z can be obtained as:

$$\begin{aligned} f_y &= 340\sqrt{(1/0.6)^2}/2 \\ &= 283 \text{ Hz} \end{aligned}$$

$$\begin{aligned} f_z &= 340\sqrt{(1/0.2)^2}/2 \\ &= 850 \text{ Hz} \end{aligned}$$

Consequently, the standing wave of the noise in the machine compartment 7 holds for the mode of the direction of Y (direction of the width) in the frequency band below the target frequency (700 Hz) and therefore, the noise produced in the machine compartment 7 may be considered a one-dimensional plane traveling wave. Consequently, the theoretical handling of the wave front can be rendered easy when the noise is to be attenuated by way of the active noise control using the speaker 13 and the like, and the attenuation control can be performed with ease and accuracy.

Referring now to FIG. 1, an acoustic signal $S_e$ generated by the microphone 14 is supplied to an adaptive control circuit 17 of the opposite phase sound producing circuit 15 to be used for the adaptive control. The principle of the adaptive control will be described with reference to FIGS. 9 to 11. The speaker 13 is adapted to receive a white noise signal from a white noise generator 19 through a switch 18. When the switch 18 is on, a white noise putting out approximately constant energy in a preselected frequency band width is produced from the speaker 13. The switch 18 is set so as to be turned on at a predetermined timing in the condition that the compressor 8 is not driven. The white noise signal from the white noise generator 19 is supplied to a first adaptive filter 20. Based on the white noise signal from the white noise generator 19 and a cancellation signal 0 from the microphone 14, an acoustic transfer signal $G_{ao}$ between the speaker 13 and the microphone 14 is measured by the first adaptive filter 20.

A vibrational sound signal M generated by the vibration sensor 12 is multiplied by the acoustic transfer signal $G_{ao}$ and then, supplied to a second adaptive filter 21. Based on a signal M $G_{ao}$ obtained by multiplying the vibrational sound signal M by the acoustic transfer signal $G_{ao}$ and the cancellation signal 0 from the microphone 14, the second adaptive filter 21 operates to obtain the difference ΔG between an acoustic transfer function G for performance of the active noise control and the latest acoustic transfer function $G_{new}$ obtained by the present adaptive control, as will be described later. In this respect, the acoustic transfer function G has an initial value or the value obtained by the last adaptive control and the acoustic transfer function $G_{ao}$ has a present value obtained by the first adaptive filter 20. In consideration of driving of the compressor 8, the vibrational sound signal M from the vibration sensor 12, the cancellation signal 0 from the microphone 14 and the sound A produced from the speaker 13 may be represented as follows:

$$M = S \cdot G_{sm} \quad (5)$$

where $G_{sm}$=an acoustic transfer function from the compressor 8 to the vibration sensor 12

$$O = S \cdot G_{so} + A \cdot G_{ao} \quad (6)$$

where $G_{so}$=an acoustic transfer function from the compressor 8 to the microphone 14

$$A = M \cdot G \quad (7)$$

Furthermore, a path from the vibration sensor 12 to the microphone 14 through the second adaptive filter 21 may be represented as follows:

$$M \cdot G_{ao} \Delta G = 0 \quad (8)$$

Expanding the equation (8), $$\begin{aligned} G &= O/(M \cdot G_{ao}) = (S \cdot G_{so} + A \cdot G_{ao}) = \\ &\quad (S \cdot G_{so} + M \cdot G \cdot G_{ao})/(M \cdot G) \\ &= (S \cdot G_{so})/(M \cdot G_{ao}) + (M \cdot G \cdot G_{ao})/(M \cdot G_{ao}) \\ &= (S \cdot G_{so})/(S \cdot G_{sm} \cdot G_{ao}) + G = (G_{so}/G_{sm})/G_{ao} + G \end{aligned}$$

Since it can be considered that $G_{so}/G_{sm} = G_{mo}$, $\Delta G = G_{mo}/G_{ao} + G$ When $G_{new}$ is considered a suitable acoustic transfer function, $$-G_{mo}/G_{ao} = G_{new}$$

Accordingly, since $\Delta G = -G_{new} + G$, $G_{new}$ can be represented as $G_{new} = G - \Delta G$. Consequently, after the acoustic transfer function G is changed to $G_{new}$, the active noise control is performed based on the acoustic transfer function $G_{new}$, whereby an optimum noise attenuating effect can be maintained with real-time coefficient changes.

Figure 9:
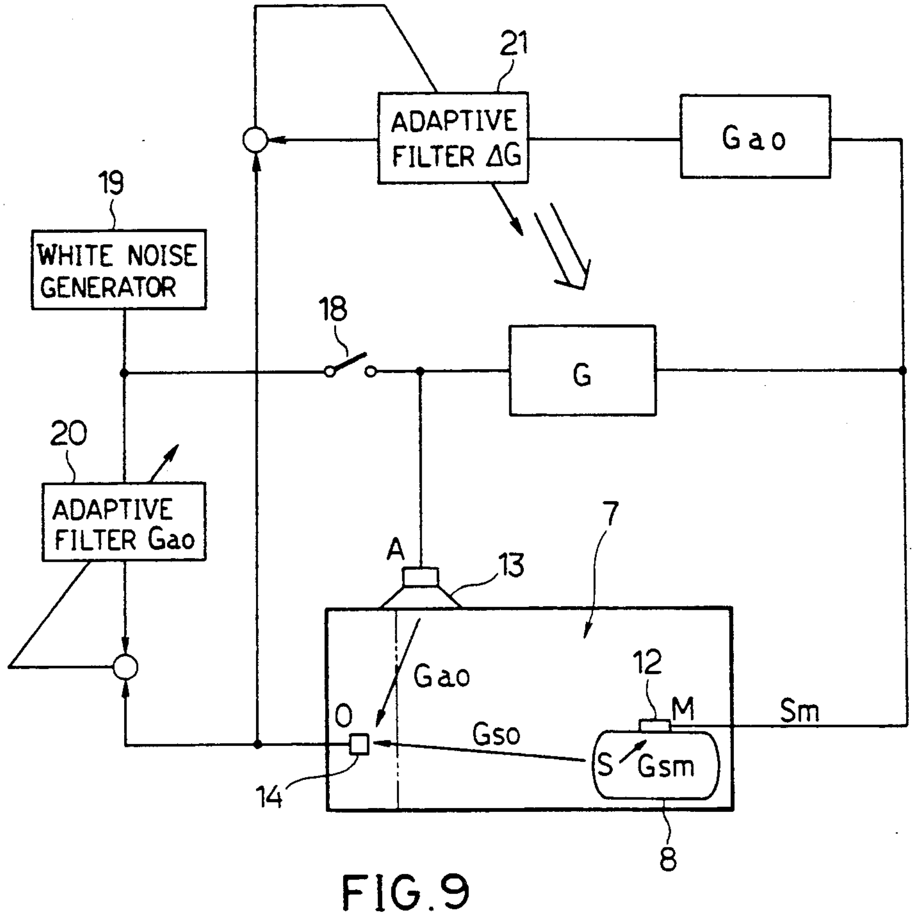
FIG. 9 is a block diagram schematically illustrating the principle of an adaptive control.
Figure 10:
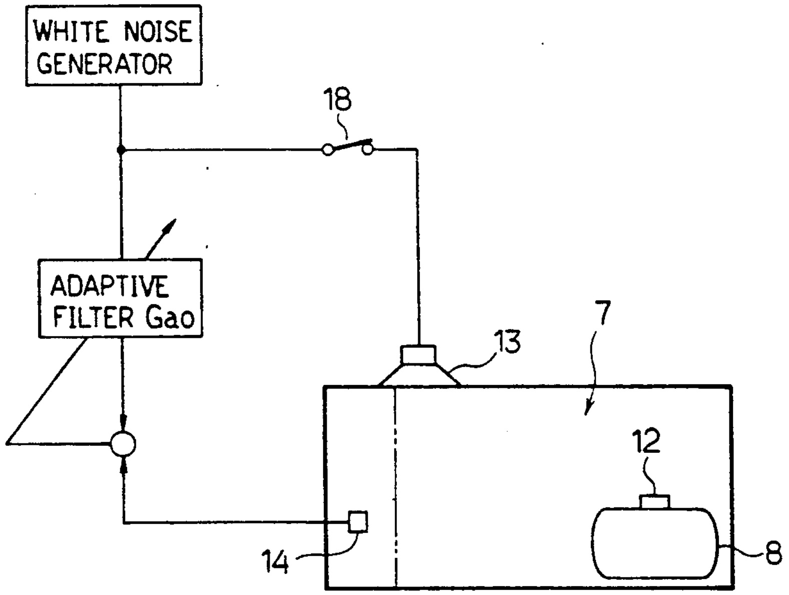
FIGS. 10 and 11 are views similar to FIG. 9 showing operations of the adaptive control, respectively.
Figure 11:
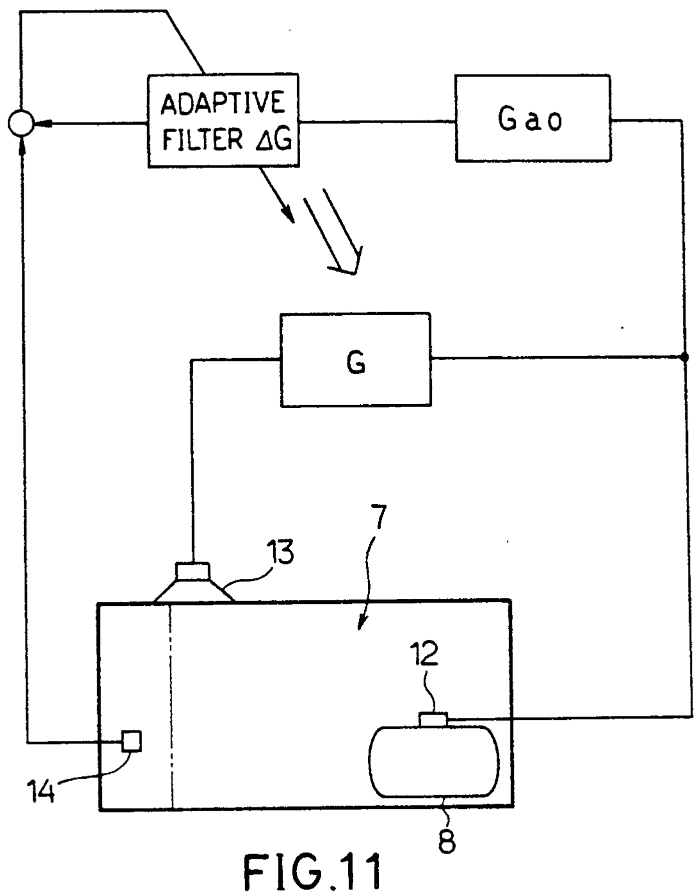

In order to actually operate an adaptive control system shown in FIG. 9, the switch 18 is turned on at the predetermined timing in the condition that the compressor 8 is not driven, as shown in FIG. 10. The white noise signal from the white noise generator 19 is supplied to the speaker 13, which produces the white noise at a predetermined level. The first adaptive filter 20 operates to obtain the acoustic transfer function $G_{ao}$ between the speaker 13 and the microphone 14, which function satisfies the acoustic transfer equation, $0=A\cdot G_{ao}$. Upon drive of the compressor 8, the second adaptive filter 21 operates to obtain $\Delta G$ based on $G_{ao}$ obtained by the first adaptive filter 20, as shown in FIG. 11. $G_{new}$ is obtained based on $\Delta G$ obtained by the second adaptive filter 21 and then, the active noise control is executed based on $G_{ao}$ obtained.

Figure 3:
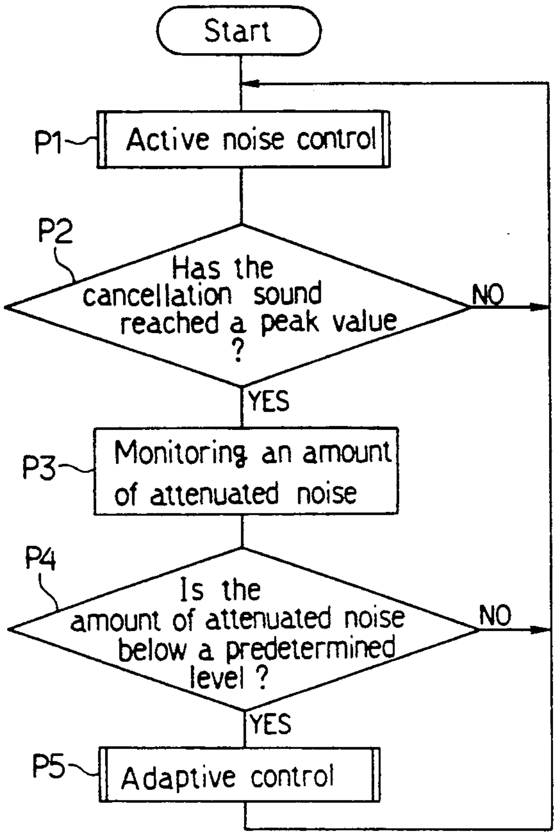
FIG. 3 is a flowchart for explaining the noise attenuating operation.

Functions of the opposite phase sound producing circuit 1 including the operational unit 16 and the adaptive control circuit 17 will now be described with reference to FIG. 3. The operational unit 16 executes an active noise control routine in which the speaker 13 is driven in accordance with the result of the operation based on the above-described active noise control principle, at a step P1, so that the artificial cancellation sound from the speaker 13 is caused to interfere with the noise from the compressor 8, thereby attenuating the noise. Such a noise attenuating operation is performed continuously. During the execution of the active noise control, the adaptive control circuit 17 operates to monitor an amount of noise attenuated by the speaker 13 based on the electrical signal $S_e$ from the microphone 14 at every timing that the artificial sound from the speaker 17 approximates to a peak value, that is, at every timing that the level of the noise from the compressor 8 periodically changing in accordance with the power supply frequency of the compressor 8 approximates to a peak value, at steps P2 and P3. Since the electrical signal $S_e$ is supplied to the control circuit 17 in synchronism with the power supply frequency, the amount of the attenuated noise indicated by the supplied electrical signal $S_e$ is escaped from an influence of an external noise and therefore, is highly reliable. The adaptive control circuit 17 operates to determine whether the amount of noise thus monitored is above or below a predetermined level, at a step P4. When the monitored amount of noise is above the predetermined level, that is, when the amount of noise attenuated by the speaker 13 is sufficient, the adaptive control circuit 17 returns to the above-described active noise control routine, at the step P1. When the monitored amount of noise is below the predetermined level or when the amount of noise attenuated by the speaker 13 is insufficient and the noise is increased, the adaptive control circuit 17 operates to perform the adaptive control routine in which an operational coefficient (acoustic transfer function) of the operational unit 16 is varied by a predetermined amount so that the amount of noise attenuated by the speaker 13 is increased, at a step P5, and thereafter, returns to the active noise control routine (the step P1).

Figure 2:
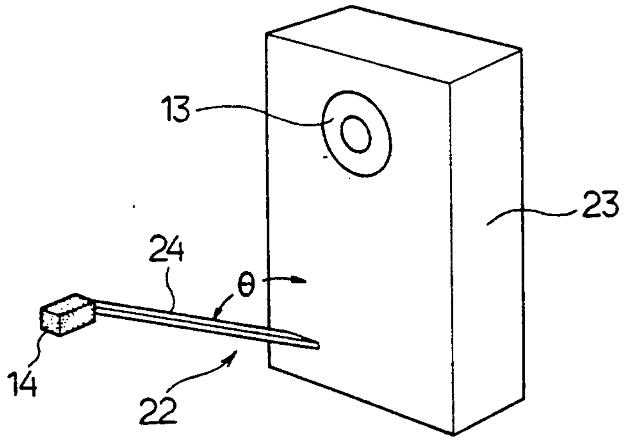
FIG. 2 is a perspective view of a cancellation sound producer and noise attenuation monitoring sound receiver integrated with the producer.

In the embodiment, the microphone 14 and the speaker 13 are integrally connected by a connecting member 22 so that occurrence in the variations of the distance between them is prevented, as shown in FIG. 2. The connecting member 22 comprises a speaker box 23 to which the speaker 13 is secured and a support arm 24 projected from the speaker box 23. The microphone 14 is secured to the distal end of the support arm 24. The speaker box 23 is embedded in an inner wall of the machine compartment 7 or the heat-insulative bottom wall of the cabinet 1. Thus, the speaker 13 and the microphone 14 are simultaneously disposed in the respective predetermined positions in the machine compartment 7. Although the speaker 13 is secured at one side of the speaker box 23 and the support arm 22 on which the microphone 14 is mounted is secured at the opposite side of the speaker box 23 to ensure the distance between the speaker 13 and the microphone 14, in the embodiment, the noise attenuation system is stable without occurrence of howling irrespective of the distance between them. Accordingly, the distance between them is determined based on the wave shape of the acoustic transfer function $G_{ao}$ (coherence function) and an amount of noise to be attenuated. The distance between them is adjusted by changing any one of the length of the support arm 24, the distance between the support arm 24 and the speaker 13 and an angle $\theta$ between the speaker box 23 and the support arm 24.

A microphone amplifier (not shown) for the microphone 14 is disposed in the speaker box 23 so that the distance or the length of a cable between the microphone 14 and the amplifier is reduced. As the sound pressure at the position of the microphone 14 is gradually reduced by the adaptive control, it becomes difficult to accurately detect a weak acoustic signal. More specifically, if the distance between the microphone 14 and the microphone amplifier is long, an electrical noise is superposed on the cable between them, which reduces accuracy of the detection of the weak acoustic signal. This causes reduction of the adaptive control accuracy and accordingly, the amount of noise attenuated is decreased. To solve this problem, the microphone amplifier is disposed in the speaker box so that the distance or length of the cable between the microphone 14 and the amplifier is reduced, as is described above. Consequently, the acoustic signal detection accuracy is improved and furthermore, the speaker box 23 interior is effectively used.

In accordance with the above-described embodiment, the speaker 13 and the microphone 14 are integrally connected with each other by the connecting member 22. Accordingly, when the speaker 13 and the microphone 14 are disposed in the machine compartment 7, these members can be disposed in the machine compartment 7 without using any specific jig with the predetermined positional relationship therebetween exactly maintained. Consequently, occurrence of the variations in the distance between the speaker 13 and the microphone 14 can be prevented, which improves the accuracy of the adaptive control. Furthermore, since the speaker 13 and the microphone 14 are simultaneously disposed in the machine compartment 7, the working efficiency can be improved as compared with the case where these members are separately disposed in the machine compartment 7, which provides the cost reduction.

Although the speaker box 23 is embedded in the heat-insulative bottom wall of the cabinet 1 in the foregoing embodiment, it may be disposed in the machine compartment 7. Furthermore, although the vibration sensor 12 is employed as the detection means for detecting the noise produced in the machine compartment 7, a microphone may be employed instead.

Figure 12:
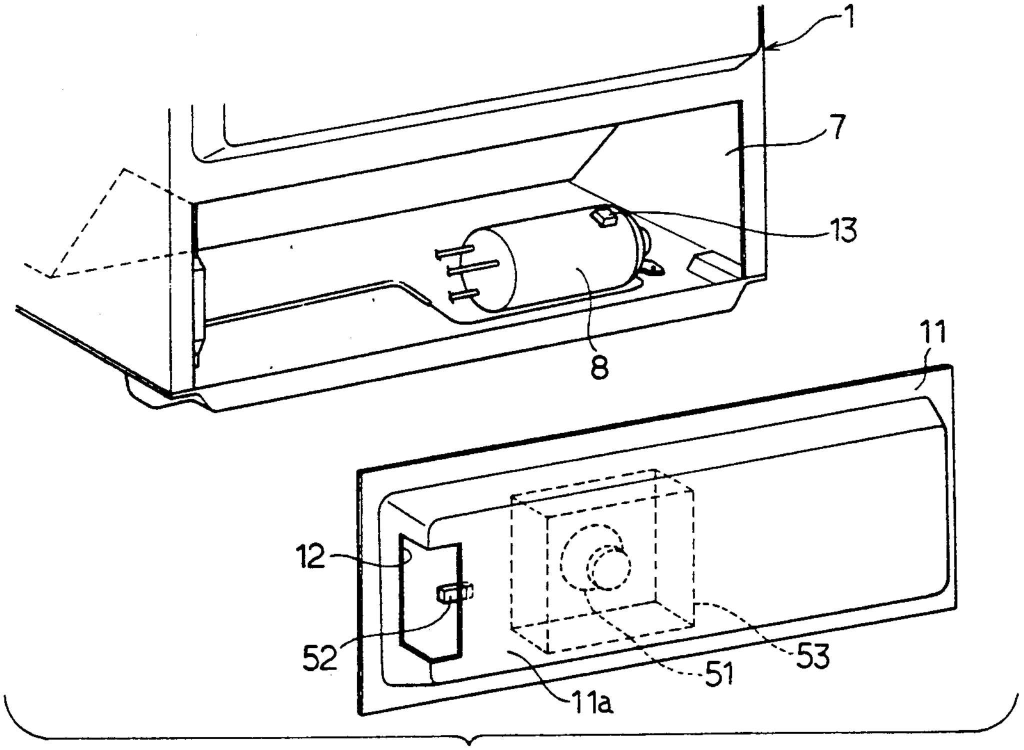
FIG. 12 is an exploded perspective view of the machine compartment to which the active noise attenuation system of a second embodiment is applied.

FIG. 12 illustrates a second embodiment of the invention. The rear cover 11 of the machine compartment 7 is utilized as the connecting member integrally connecting the active noise control speaker 51 and the noise attenuation monitoring microphone 52. The speaker box 53 of the speaker 51 and the microphone 52 are mounted at respective predetermined positions on the inside of the rear cover 11. The other construction is the same as that in the foregoing embodiment.

In accordance with the second embodiment, the rear cover 11 serves as the connecting member integrally connecting the speaker 51 and the microphone 52. Accordingly, the same effect can be achieved as in the foregoing embodiment. Furthermore, since the speaker 51 is not embedded in the heat-insulative bottom wall of the cabinet 1, the thickness of the cabinet bottom wall need not be increased and the compartment volume of the cabinet 1 is prevented from being reduced. Furthermore, even if the compressor 8 and the complicated piping are provided in the machine compartment 7, the inspection and maintenance for the speaker 51 and the microphone 52 may be readily performed when the rear cover 11 is detached. Since the provision of the above-described noise attenuation system does not necessitate alteration of the construction of the heat-insulative cabinet 1, an excessive cost is not needed. When the design of the machine compartment 7 is standardized, the noise attenuation system may be applied to the refrigerators of the different types.

Although the noise attenuation system is applied to the household refrigerator in the foregoing embodiments, it may be applied to an outdoor unit of a room air conditioner or a refrigerative show case.

The foregoing disclosure and drawings are merely illustrative of the principles of the present invention and are not to be interpreted in a limiting sense. The only limitation is to be determined from the scope of the appended claims.

We claim:

1. A refrigerating apparatus having noise, attenuation comprising:

- a heat-insulative cabinet having a storage compartment and a machine compartment;
- a compressor provided in the machine compartment;
- sound detection means, provided in the machine compartment, for detecting noise produced by operating the compressor and converting the detected noise to a corresponding electrical signal, the detected noise having a first phase;
- an operational unit, electrically coupled to the sound detection means, for converting the electrical signal provided by the sound detection means to an acoustic signal to perform active noise control;
- a cancellation sound producer for producing, responsive to the acoustic signal, a sound having a second phase opposite to the first phase of the noise to attenuate the noise;
- a noise attenuation monitoring sound receiver for monitoring a noise attenuating effect of the cancellation sound producer and providing an attenuation value relating to the noise attenuating effect;
- an adaptive control circuit, electrically coupled between the noise attenuation monitoring sound receiver and the operational unit, for adjusting an operating condition of the operational unit by a predetermined amount when the attenuation value is out of a predetermined tolerance, the adaptive control circuit repeatedly adjusting the operating condition of the operational unit until the attenuation value comes within the predetermined tolerance; and
- means for fixing the cancellation sound producer and the noise attenuation monitoring sound receiver at a first predetermined distance apart.

2. A refrigerating apparatus according to claim 1, wherein the fixing means is a rear cover, detachably mounting to the refrigeration apparatus, to cover a rear opening of the machine compartment.

3. A refrigerating apparatus according to claim 1, wherein the cancellation sound producer is embedded in an heat-insulative wall defining the machine compartment.

4. A refrigerating apparatus according to claim 1, wherein the sound detection means comprises a vibration sensor mounted on the compressor.

5. A refrigeration apparatus according to claim 1, wherein the machine compartment is defined by first, second and third dimensions, the first dimension being larger than the second and the third dimensions to cause the sound to form a standing wave propagating in the direction of the first dimension.

6. A refrigerating apparatus according to claim 2, wherein the rear cover of the machine compartment has a ventilating opening formed therein at a second predetermined distance away from the compressor and the noise attenuation monitoring sound receiver is disposed proximate to the ventilating opening in.

7. A refrigerating apparatus according to claim 2, wherein the rear cover of the machine compartment comprises material having predetermined heat-conductivity and predetermined sound-transfer loss properties.

* * * * *